United States Patent [19]

Feingold

[11] 4,233,987
[45] Nov. 18, 1980

[54] CURVILINEAR ELECTROCARDIOGRAPH ELECTRODE STRIP

[76] Inventor: Alfred Feingold, 5310 Maggiore St., Coral Gables, Fla. 33146

[21] Appl. No.: 934,854

[22] Filed: Aug. 18, 1978

[51] Int. Cl.³ .............................................. A61B 5/04
[52] U.S. Cl. .................................................... 128/639
[58] Field of Search ............... 128/2.06 E, 2.1 E, 404, 128/410, 411, 416–418, DIG. 4, 639–641, 643, 644, 798, 802, 803, 791, 792, 783

[56] References Cited

U.S. PATENT DOCUMENTS

| | | | |
|---|---|---|---|
| 2,943,628 | 7/1960 | Howell | 128/418 |
| 3,151,619 | 10/1964 | Sullivan | 128/417 |
| 3,380,445 | 4/1968 | Frasier | 128/2.06 E |
| 3,387,608 | 6/1968 | Figar | 128/418 X |
| 3,409,007 | 11/1968 | Fuller | 128/2.06 E |
| 3,971,387 | 7/1976 | Mantell | 128/410 |
| 4,026,278 | 5/1977 | Ricketts et al. | 128/2.06 E |
| 4,121,575 | 10/1978 | Mills et al. | 128/2.06 E |

FOREIGN PATENT DOCUMENTS 122258 2/1972 Denmark ............................ 128/2.06 E
274612 7/1951 Switzerland ........................... 128/644

OTHER PUBLICATIONS

Richardson et al., "Some New Electrode Techniques . . .", Aerospace Medicine, Jul. 1968, pp. 745–750.

*Primary Examiner*—Lee S. Cohen
*Attorney, Agent, or Firm*—Cook, Wetzel & Egan, Ltd.

[57] ABSTRACT

Electrodes as for use in taking electrocardiograms are provided in a multiple electrode pad formed as an elongate, narrow, curved strip with the electrodes arranged in a curvilinear relation to one another. The pad readily assumes the shape of the thorax or chest of a man, woman, or child at several desirable application sites, such as precordially, for routine or emergency use. The strip may be perforated or otherwise weakened in lines between the electrodes for tearing of the strip to separate the electrodes for individualized placement.

5 Claims, 5 Drawing Figures

CURVILINEAR ELECTROCARDIOGRAPH ELECTRODE STRIP

The present invention relates to multiple electrode pads, particularly pads for use in taking electrocardiograms wherein a plurality of electrical signals in a patient's body are monitored through his skin.

Multiple electrode pads have commonly been used to facilitate simultaneous placement of a plurality of electrodes upon a patient's skin. Commercial embodiments of such electrode pads known to the inventor are provided as flexible rectangular foam or similar pads, each with one electrode at each of four corners. Such pads are suitable for use only on relatively flat surfaces of a patient's body, such as the middle or upper part of the back. However, such position is not always readily available for use, as in some types of surgery and in emergency use upon a supine patient. For such uses individual electrodes must be employed. Different size pads have been employed for adults and for children. Further, the known prior art devices are not suited to separation of any one electrode from a multiple electrode pad for use in special circumstances.

According to the present invention, a multiple electrode pad is formed as a thin, flexible, relatively narrow, flat, and elongate strip curved in the plane of its flat surface. The pad is fitted with a plurality of electrodes arranged on one face of the stip in a spaced-apart curvilinear relation to one another. The electrodes may be separated from one another by tearing the strip into sections along perforations or other lines of weakened material between the electrodes. The shape of the pad permits the pad to be applied effectively, without stretching or distortion, to any curved portion of the chest or thorax of a patient of any age or size.

As is known in the art, each of the individual electrodes of the strip is surrounded by a pressure-sensitive adhesive film bonded to the material of the pad; the adhesive is covered until ready for use by a protective paper. Electric contact between a wire leading to the monitoring station and the patient's skin is effected by a conductive jelly or cream.

Figure 1:
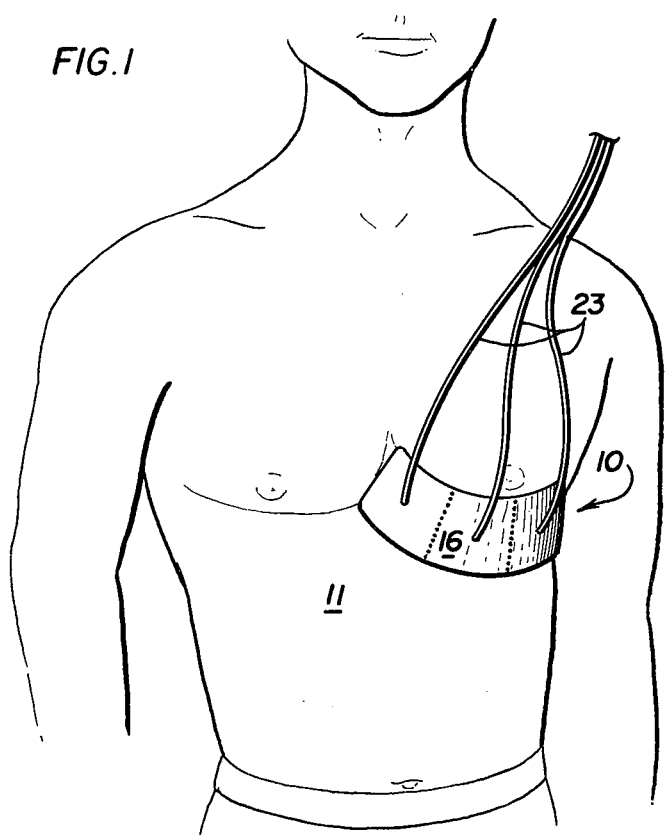
FIG. 1 is a perspective view of one embodiment of the device applied to a patient's chest at a precordial site.

A multiple electrode pad 10 in accordance with the invention is shown in FIG. 1 applied to the chest or thorax 11 of a patient at a precordial site, beneath the left breast. The patient's skin is substantially curved at this position. Large, rectangular pads are not suited to such placement, although the position is desirable, especially as for use on a supine patient, to monitor heart activity.

Figure 2:
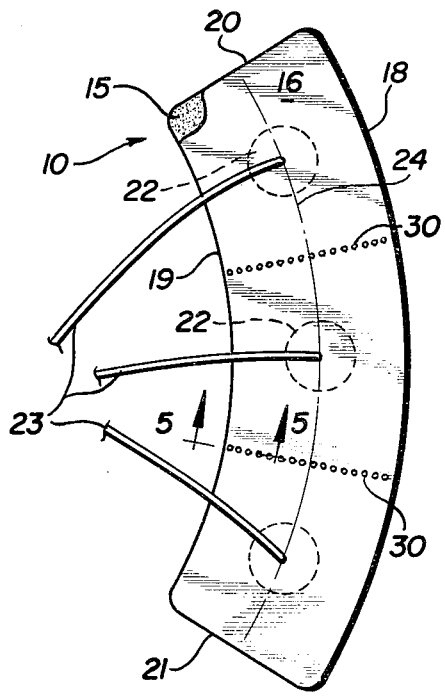
FIG. 2 is a top plan view of the multiple electrode strip of FIG. 1.
Figure 3:
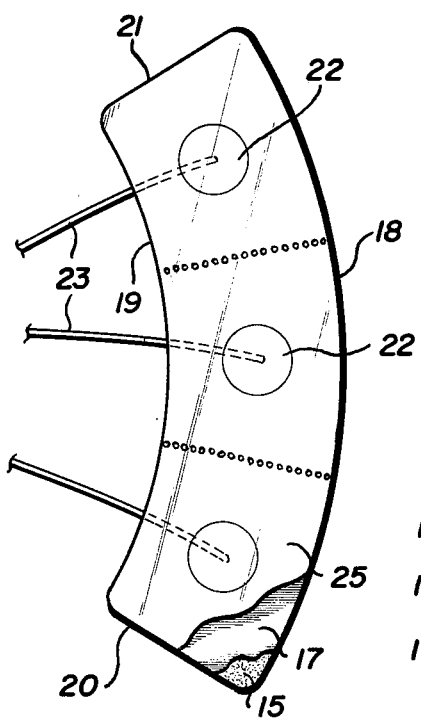
FIG. 3 is a bottom plan view of the electrode strip of FIG. 2.

The multiple electrode pad 10 is formed as an elongate, narrow strip as shown in FIGS. 2 and 3. The electrode pad 10 comprises a foam or other thin, flexible material core 15 having opposite flat faces. A covering 16 is applied to an upper one of the faces in this first embodiment, and an adhesive film 17 to the other, lower face. The opposite faces of the pad core 15 are bounded by a common edge or edges having sides 18, 19, 20, and 21.

A plurality of individual electrode elements 22 are carried in the core 15 of the strip 10, in a manner known in the art. Each electrode element 22 is surrounded by the pressure-sensitive adhesive film 17 covering some or all of the lower face of the pad core 15. Contact between the electrode 22 and the skin of the patient is completed by application of a conductive jelly or cream contacting metal portions of the electrode element and the skin of the patient at the application site. Electric wires 23 connect from the metal parts of the electrodes 22 through a plug, not shown, to a monitoring apparatus comprising a cathode ray tube and/or a paper tape or other output. The electrodes 22 are spaced apart along the strip or pad 10 on a curvilinear line 24, which may be substantially an arc of a circle as shown or any other desired regular or irregular curve.

Further in accordance with the principles of the invention, each of the electrodes 22 may be separated from the adjacent electrode(s) in the strip 10 by a line of weakened material 30 formed in the core 15 and covering layers. Perforations as shown in FIG. 2 or any similar material treatment may be used to form the lines 30, such as cutting of the material mostly through its thickness or, especially if the material 15 is a plastic foam, melting the material to weaken it along selected lines. The lines 30 of weakened material are generally perpendicular to the curvilinear line 24. Severing of any of the electrodes 22 from one another if desired for individualized placement of electrodes on the chest 11 of a patient is accomplished by tearing or cutting of the material 15 along any of the lines 30. The wires 23 may be separated from one another by pulling their insulating coverings apart to the needed free lengths, if necessary.

Figure 4:
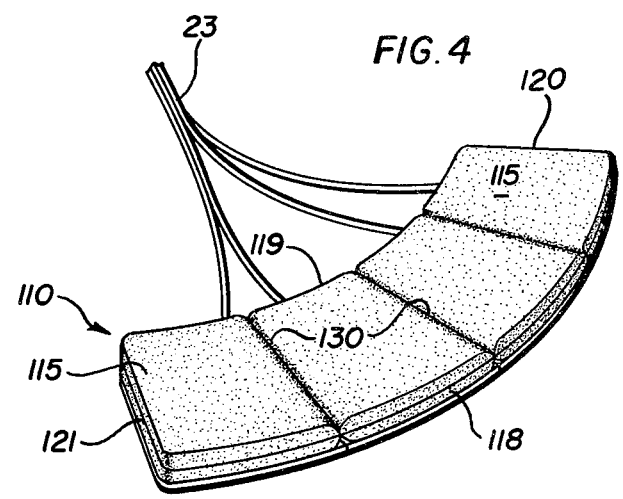
FIG. 4 is a perspective view of a second embodiment of the invention.

FIG. 4 shows a second form of the invention, wherein four electrodes 22 are employed within an electrode strip 110 constructed from a foam material 115 with sides 118, 119, 120, and 121 as shown, sides 118 and 119 being curved in the plane of the pad 110. Two layers of foam glued together are conveniently employed to sandwich the connecting wires 23 from the electrodes and to direct them out the edge 119 of the pad 110. No upper covering as 16 in FIG. 2 is employed. Lines 130 of weakened material are formed in the material 115 between the electrodes 22 in the FIG. 4 embodiment by severing the material most of the way through or by melting same to weaken the material, as shown, or by some other process. Then the individual electrodes can be separated from one another for individual application merely by tearing the desired electrode or electrodes from the strip 110.

Figure 5:
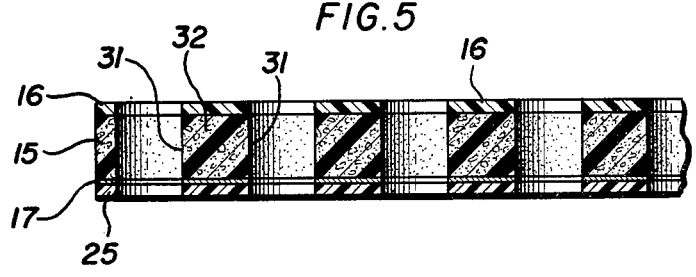
FIG. 5 is a sectional view, taken on line 5—5 of FIG. 2.

FIG. 5 shows in detail the perforations along the line 30 of the embodiment of FIG. 2, wherein the material 15 of the pad 10 together with top covering 16, the adhesive film 17 and a protective paper 25 are punched through by cylindric or other-shape punches to form apertures 31 through such materials. The remaining portions 32 between the apertures 31 can readily be torn or sheared without using special tools.

A multiple electrode strip 10 or 110 of the invention is used substantially as any known pad, except that the strip may be applied to a curved body surface. The application site is selected and cleansed. The protective paper 25 is removed from the adhesive 17 and conductive jelly is applied to the electrode if it was not preapplied. The strip 10 or 110 is then positioned on the application site and pressed gently to create an adhesive connection. In special circumstances any of the electrodes 22 can be separated from the others of the strip 10 by severing the strip on one of the weakened lines 30 or 130 and repositioning the individual electrode as desired within the area permitted by its wire 23, with or without tearing of the insulation to separate such wire from the others of the cable.

Although various minor modifications may be suggested by those familiar with the art and may adapt the present invention with various modifications, it should be understood that I wish to embody within the scope of the patent warranted hereon all such modifications as reasonably and properly come within the scope of my contribution to the art.

I claim as my invention:

1. An electrode pad comprising a thin, flexible, narrow, generally flat, and elongate strip having two opposite faces bounded by common edges including two curvilinear edges opposite one another and extending the elongate length of the strip, the pad being adapted to be applied to the chest or thorax of a patient as for electrodcardiography, wherein the strip carries a plurality of electrodes spaced apart along such strip on one face thereof, whereby the strip may readily and without stretching assume the curved contour of a patient's body upon application of said strip thereto.

2. An electrode pad as defined in claim 1, wherein the strip is formed with a line of weakened material extending substantially from one face to the other through the strip and from one curvilinear edge to the other across the strip and between adjacent electrodes, whereby to facilitate separation of the electrodes of the pad as by tearing for individualized placement of each of said electrodes.

3. An electrode pad as defined in claim 1 or claim 2, wherein the strip carries at least three electrodes and the electrodes are spaced in a curvilinear relation to one another along the strip.

4. An electrode pad comprising a flexible, generally flat material with opposite faces and formed as a strip and bearing a plurality of electrodes, the pad having two opposite generally flat surfaces comprising said opposite faces, said surfaces being bounded by common edges including two opposite generally parallel curvilinear sides, wherein the pad is adapted for application to curved portions of the chest or thorax of a patient, and wherein:

the pad is formed as an elongate, narrow strip carrying on one of its surfaces at least three electrodes; and the electrodes are spaced apart from one another on such strip along a curved line which extends generally parallel to and between the curvilinear sides of the pad, whereby to facilitate application to a patient.

5. An electrode pad as defined in claim 4, wherein any of said electrodes is separable from an adjacent electrode via a line of weakened material extending through and across the pad between said electrode and said adjacent electrode and wherein each said electrode has a conductive wire integrally attached thereto, said wire engaging the electrode pad only on a side of the weakened line adjacent such electrode, whereby fully to facilitate separation of such electrode from the rest of the electrodes in said pad.

* * * * *